United States Patent [19]

Alexander et al.

[11] 4,402,612
[45] Sep. 6, 1983

[54] APPARATUS FOR DETECTING FOREIGN PARTICLES IN A LIQUID

[76] Inventors: Jury V. Alexander, ulitsa Fontanka, 165, kv. 13; Viktor D. Viktorov, Basseinaya ulitsa, 105, kv. 480; Vladimir K. Zuev, ulitsa Sofiskaya, 48, Korpus 1 kv. 164; Gennady S. Orlov, ulitsa Aviatsionnaya, 36, kv. 10; Nikolai A. Filipin, ulitsa Nalichnaya, 36, kv. 110, all of Leningrad; Fedor S. Khunafin, ulitsa Fadeeva, 6, kv. 87, Moscow, all of U.S.S.R.

[21] Appl. No.: 207,243

[22] Filed: Nov. 17, 1980

[51] Int. Cl.³ ............................................. G01N 21/90
[52] U.S. Cl. ..................................... 356/427; 356/240; 358/106
[58] Field of Search ........................... 250/223 B, 574; 356/427, 428, 240, 250; 358/106; 209/524

[56] References Cited

U.S. PATENT DOCUMENTS 4,025,201  5/1977  Deane ................. 356/240
4,063,823 12/1977  Grat .................... 356/427

FOREIGN PATENT DOCUMENTS 52-36411  3/1977  Japan ................... 358/106
1244744   9/1971  United Kingdom .

Primary Examiner—Vincent P. McGraw
Attorney, Agent, or Firm—Lilling & Greenspan

[57] ABSTRACT

The apparatus for detecting foreign particles in a liquid, includes a radiation source for irradiating the inspected zone of the liquid, and a television camera including a projecting system for projecting the image of the inspected zone of the liquid on the target of a pickup tube. The projecting system comprises a means for superposing the images of different areas of the inspected zone of the liquid.

4 Claims, 2 Drawing Figures

APPARATUS FOR DETECTING FOREIGN PARTICLES IN A LIQUID

FIELD OF THE INVENTION

The present invention relates to apparatuses for automatically inspecting liquid materials and, more particularly to apparatuses for detecting foreign particles in a liquid.

The present invention can be used for detecting foreign particles in liquids contained in transparent containers. The present invention can most advantageously be used in apparatuses for testing the quality of foodstuffs and pharmaceutical materials.

DESCRIPTION OF THE PRIOR ART

Detection of foreign particles in a liquid may be carried out by placing the liquid to be inspected in the path of a beam produced by a radiation source, such as light source, bringing into suspension the particles present in the liquid, e.g., by rotating the liquid filled container, and converting the radiation scattered by the particles into an electrical signal.

Known in the art is an apparatus for detecting foreign particles in a liquid, comprising a mechanism for bringing particles into suspension, a radiation source for irradiating the inspected zone of the liquid, a radiation receiving device, and a register means for registering the output signal of the radiation receiving device, the radiation receiving device including a sensing element and a projecting system for projecting the image of the inspected zone of the liquid on the target of the sensing element (cf. Great Britain Pat. No. 1,244,744). In that apparatus the radiation receiving device is a television camera, which makes it possible to estimate dimensions of individual particles and to reject the liquids containing particles the size of which exceeds a predetermined limit.

With given dimensions of the target of the sensing element of the radiation receiving device, e.g., of the target of a television pickup tube, the minimum size of the particles which can be detected is determined by the sensitivity of the radiation receiving device and by the size of the liquid zone to be inspected. The larger the inspected zone the greater is the minimum size of the particles which can be detected. Therefore, if very small particles must be detected, the volume of the liquid which can be inspected at a time with the known apparatus is relatively small. For example, if the pickup tube having target dimensions of 9×12 mm and a raster of 625 lines is used and if particles having a minimum size as small as 15 microns must be detected, the maximum dimension of the zone of the liquid which can be inspected at a time is about 1 cm. This is usually much smaller than the whole volume of the liquid containing the foreign particles, which makes it difficult to provide reliable testing of the liquid.

A somewhat more reliable detection of foreign particles may be achieved if the lowermost portion of the liquid is inspected. This, however, leads to an increase in the inspection time because of the need to wait until the suspended particles sink and enter the inspected zone. Besides, the particles having a density less than, or close to, the density of the liquid may not enter the inspected zone at all.

Therefore the known apparatus does not provide for quick and reliable detection of small-sized foreign particles in a liquid. The principal object of the present invention is to provide an apparatus for detecting foreign particles in a liquid, which is designed so as to enlarge the liquid zone inspected simultaneously and thus to ensure a more rapid and reliable detection of small-sized foreign particles.

SUMMARY OF THE INVENTION

Accordingly, it is an object of the present invention to provide an apparatus for detecting foreign particles in a liquid, which ensures a more rapid detection of small-sized foreign particles.

Another object of the present invention is to provide an apparatus for detecting foreign particles in a liquid, which ensures a more reliable detection of small-sized foreign particles.

Still another object of the present invention is to provide an apparatus for detecting foreign particles in a liquid which is designed so as to enlarge the liquid zone inspected simultaneously.

With these and other objects in view, there is proposed an apparatus for detecting foreign particles in a liquid, comprising a mechanism for bringing the particles into suspension, a radiation source for irradiating the inspected zone of the liquid, a radiation receiving device, and a register means for registering the output signal of the radiation receiving device, the radiation receiving device including a sensing element and a projecting system for projecting the image of the inspected zone of the liquid on the target of the sensing element according to the invention, the projecting system comprises a means for superposing the images of different areas of the inspected zone of the liquid.

Such an apparatus makes it possible to increase the dimensions of the inspected zone of the liquid without the need for increasing the size of the target of the sensing element of the radiation receiving device or the sensitivity thereof and thus to ensure a more rapid and reliable detection of foreign particles having a small size.

The means for superposing the images may comprise two flat parallel reflecting surfaces facing each other and positioned between the target of the sensing element and the objective lens of the projecting system, the reflecting surfaces being parallel to the axis of the objective lens.

To compensate for the losses caused by reflection of radiation from the reflecting surfaces a radiation filter can be used which is positioned between the radiation source and the objective lens of the projecting system and is made so that the transparency of its portions traversed by the rays falling on the target of the sensing element of the radiation receiving device after being reflected from a reflecting surface of the means for superposing the images is greater than the transparency of the portion of the filter traversed by the rays falling on the target of the sensing element directly through the lens without reflection from a reflecting source, and the transparency of the portions of the filter traversed by the rays falling on the target of the sensing element after a greater number of reflections is greater than the transparency of the portions traversed by the rays falling on the target of the sensing element after a smaller number of reflections.

According to another embodiment of the invention compensation for the losses caused by reflection of radiation from the reflecting surfaces may be achieved by using several radiation sources positioned so that the intensity of radiation incident on that area of the inspected zone of the liquid the image of which is projected on the target of the sensing element of the radiation receiving device directly through the objective lens without reflection from a reflecting surface of the means for superposing the images is less than the intensity of radiation incident on that area of the inspected zone the image of which is projected on the target of the sensing element after being reflected from a reflecting surface, and the intensity of radiation incident on that area of the inspected zone the image of which is projected on the target of the sensing element after being reflected is the greater, the greater is the number of reflections undergone by the image of this area before being projected on the target of the sensing element.

The above-mentioned and other objects and advantages of the present invention will become more apparent upon consideration of the following detailed description of its preferred embodiments taken in conjunction with the accompanying drawings.

DETAILED DESCRIPTION OF THE INVENTION

Figure 1:
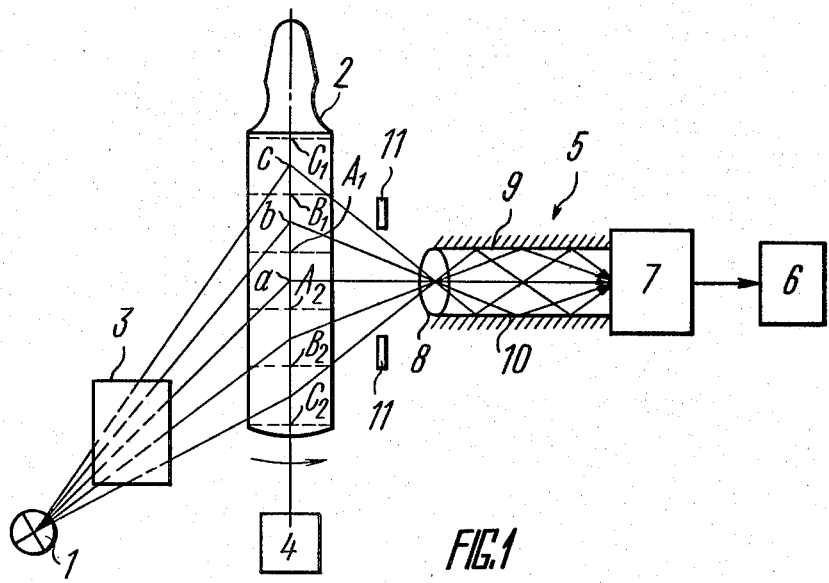
FIG. 1 shows a schematic arrangement of an apparatus for detecting foreign particles in a liquid, according to the invention.

According to FIG. 1, the apparatus for detecting foreign particles in a liquid comprises an optical radiation source 1 for illuminating the liquid in a container 2, and an optical filter 3 positioned between the source 1 and the container 2 and having a transparency varying along the height of the filter 3. The apparatus further comprises a mechanism 4 for setting the container 2 in rotation, a radiation receiving device constituted by a television camera 5, and a register means 6 for registering the signal at the output of the television camera 5.

The television camera 5 comprises a pickup tube 7, representing the sensing element of the radiation receiving device, and a projecting system for projecting the image of the inspected zone of the liquid in the container 2 on the target of the sensing element of the radiation receiving device, i.e., on the target of the pickup tube 7. The projecting system comprises an objective lens 8 positioned between the container 2 and the target of the pickup tube 7, and a means for superposing the images of different areas of the inspected zone of the liquid, said means including two flat parallel mirrors 9 and 10 positioned between the lens 8 and the target of the tube 7 so that their reflecting surfaces face each other and are parallel to the optical axis of the lens 8. A diaphragm 11 is positioned between the lens 8 of the television camera 5 and the container 2.

During inspection the container 2 is set in rotation around its vertical axis, which is followed by braking, whereby the foreign particles present in the liquid are brought into suspension. The light from the source 1 through the optical filter 3 falls on the container 2 illuminating the liquid therein. The presence of foreign particles in the liquid leads to scattering of the light produced by the source 1. The light scattered by the particles falls on the target of the pickup tube 7 through the lens 8 which provides focusing of the rays scattered by the particles located in the vertical plane passing through the axis of the container 2 on the target of the pickup tube 7. The diafragm 11 serves to prevent the light scattered by the bottom of the container 2 and by the meniscus of the liquid from falling on the target of the tube 7.

The rays scattered by the particles located in the central area of the vertical plane whose image is focused on the target of the pickup tube 7, i.e., in the area located between points $A_1$ and $A_2$, fall on the target of the tube 7 directly through the lens 8 without reflection from the mirror 9 or 10. In FIG. 1 there is shown the passage of one of the rays scattered by the particle located at a point "a" of the area $A_1A_2$, i.e., of the ray which passes through the center of the lens 8. The rays scattered by the particles located in the area $A_1A_2$ above and below the point "a" will be respectively focused below and above the point of focusing of the rays scattered by the particle located at the point "a".

The rays scattered by the particles located in the area of the above-mentioned vertical plane and above the area $A_1A_2$, i.e., in the area located between the point $A_1$ and a point $B_1$, fall on the target of the tube 7 after being reflected from the lower mirror 10. In FIG. 1 there is shown the passage of one of the rays scattered by the particle located at a point "b" of the area $A_1B_1$. The rays scattered by the particles located in the area $A_1B_1$ above and below the point "b" will be, after being reflected from the mirror 10, respectively focused above and below the point of focusing of the rays scattered by the particle located at the point "b".

The rays scattered by the particles located in the area above the area $A_1B_1$, i.e., in the area located between the point $B_1$ and a point $C_1$, fall on the target of the tube 7 after being reflected first from the lower mirror 10 and then from the upper mirror 9. In FIG. 1 there is shown the passage of one of the rays scattered by the particle located at a point "c" of the area $B_1C_1$. The rays scattered by the particles located in the area $B_1C_1$ above and below the point "c" will be, after being reflected first from the mirror 10 and then from the mirror 9, respectively focused below and above the point of focusing of the rays scattered by the particle located at the point "c".

Likewise, the rays scattered by the particles located in the area below the central area $A_1A_2$, i.e., in an area $A_2B_2$, fall on the target of the tube 7 after being reflected from the upper mirror 9, and the rays scattered by the particles located in an area $B_2C_2$ located below the area $A_2B_2$ fall on the target of the tube 7 after being reflected first from the upper mirror 9 and then from the lower mirror 10.

Thus the mirrors 9 and 10 provide a means for superposing the images of the areas $A_1A_2$, $A_1B_1$, $A_2B_2$, $B_1C_1$ and $B_2C_2$ of the inspected zone when they are projected on the target of the pickup tube 7. If any particles are present in the neighborhood of these areas, the images of these particles will be focused at corresponding points of the target of the tube 7; the intensity of the light scattered by a particle and focused at a corresponding point of the target being the greater, the greater is the size of the particle. The falling of the focused rays scattered by a particle on the target of the tube 7 produces a pulse at the output of the television camera 5, said pulse being registered by the register means 6 if the amplitude of the pulse is above a predetermined level corresponding to the smallest of the particles to be detected. Therefore, the employment of the mirrors 9 and 10 allows an increase of several times of the dimensions of the liquid zone which can be inspected at a time. In so doing there is no need to increase the focal length of the lens 8 and thus to decrease the size of the particle images on the target of the tube 7, which would have made it necessary to increase the sensitivity and resolution of the camera 5. There is also no need to increase the dimensions of the target of the tube 7.

The optical filter 3 has a transparency varying along its height so that the transparency of its portions traversed by the rays illuminating the areas $A_1B_1$ and $A_2B_2$ of the inspected zone is greater than the transparency of the portion traversed by the rays illuminating the area $A_1A_2$ of the inspected zone, and the transparency of the portions of the filter 3 traversed by the rays illuminating the areas $B_1C_1$ and $B_2C_2$ of the inspected zone is greater than the transparency of the portions traversed by the rays illuminating the areas $A_1B_1$ and $A_2B_2$. The differences in the transparencies of these portions of the filter 3 is such that the intensity of the light illuminating the areas $A_1B_1$ and $A_2B_2$ exceeds the intensity of the light illuminating the area $A_1A_2$ by a value that ensures compensation for the energy losses caused by a single reflection from the mirror 9 or 10, and the intensity of the light illuminating the areas $B_1C_1$ and $B_2C_2$ exceeds the intensity of the light illuminating the areas $A_1B_1$ and $A_2B_2$ by a value that ensures compensation for the energy losses caused by a double reflection, i.e., first from the mirror 9 and then from the mirror 10 or vice versa. This ensures the same amplitude of the pulses produced at the output of the television camera 5 in response to the light falling on the target of the tube 7 from the particles of the same size irrespective of the area of the inspected zone in which they are located.

The variable transparency filter 3 may be positioned between the container 2 and the objective lens 8 of the television camera 5. In such a case the inspected zone of the liquid is uniformly illuminated, the compensation for the energy losses caused by reflection from the mirrors 9 and 10 being achieved by reduction in the intensity of the light scattered by the particles located in the area $A_1A_2$ with respect to the intensity of the light scattered by the particles located in the areas $A_1B_1$ and $A_2B_2$, and by reduction in the intensity of the light scattered by the particles located in the areas $A_1B_1$ and $A_2B_2$ with respect to the intensity of the light scattered by the particles located in the areas $B_1C_1$ and $B_2C_2$.

If necessary, the number of the areas the images of which are superposed can be increased by using the rays falling on the target of the tube 7 after undergoing three or more successive reflections from the mirrors 9 and 10.

Figure 2:
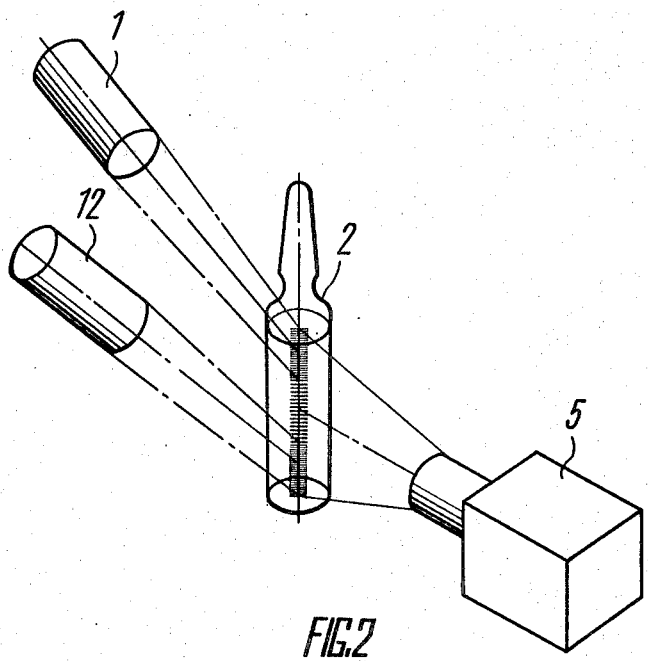
FIG. 2 shows an arrangement of the elements of the apparatus for detecting foreign particles in a liquid with the use of two radiation sources.

Non-uniform illumination of different areas of the inspected zone may be achieved by other means. Thus, if three different areas of the inspected zone are to be superposed when projected on the target of the pickup tube 7, two radiation sources may be used, as shown in FIG. 2. According to FIG. 2, the apparatus for detecting foreign particles in a liquid further comprises an additional optical radiation source 12, the radiation sources 1 and 12 being directional sources and positioned so that the source 1 illuminates the uppermost area of the inspected zone of the liquid, the image of which is projected on the target of the tube 7 (FIG. 1) after being reflected from one of the surfaces 9 or 10, while the source 12 (FIG. 2) illuminates the lowermost area of the inspected zone, the image of which is projected on the target of the tube 7 (FIG. 1) after being reflected from the other of the mirrors 9 or 10. Illumination of the central area of the inspected zone is effected through diffusion of the light from the sources 1 (FIG. 2) and 12 in the liquid. As a result, the intensity of the light illuminating the central area of the inspected zone is smaller than the intensity of the light illuminating its upper and lower areas, which provides compensation for the energy losses caused by reflections from the mirrors 9 and 10.

If more than three different areas of the inspected zone projected on the target of the tube 7 (FIG. 1) are superposed, a greater number of radiation sources illuminating said zone may be employed so as to ensure a greater intensity of radiation incident on the area of the inspected zone which undergoes a greater number of reflections before being projected on the target of the tube 7.

While the invention is described herein in the terms of the preferred embodiments, numerous modifications may be made without departure from the spirit and scope of the invention as defined by the appended claims.

It will be clear that instead of the flat parallel mirrors 9 and 10 other means for superposing the projected images may be employed. Such a means may include, for example, a triangular prism positioned between the container and the objective lens of the projecting system and two tilted mirrors positioned so that the rays scattered by the particles located in the upper area of the inspected zone fall on the target of the radiation receiving device after being reflected from one of the mirrors and one of the sides of the prism, while the rays scattered by the particles located in the lower area of the inspected zone fall on the target of the radiation receiving device after being reflected from the other mirror and the other side of the prism. It is also possible to use a beam-splitting prism and a mirror which are so positioned that the rays scattered by the particles located in one of the areas of the inspected zone fall on the target of the radiation receiving device after passing through the beam splitting surface of the prism, while the rays scattered by the particles located in another area of the inspected zone fall on the target of the radiation receiving device after being reflected from the mirror and the beam-splitting surface.

If necessary, the optical radiation source 1 and the television camera 5 may be respectively substituted by a source and a receiver of another type of radiation, such as ultra-high frequency radiation, X-rays, etc.

I claim:

1. An apparatus for detecting foreign particles in a liquid, comprising:
 a mechanism for bringing said particles into suspension;
 a radiation source irradiating the inspected zone of said liquid;
 a radiation receiving device having an output and including a sensing element having a target; and
 a projecting system projecting the image of said inspected zone of the liquid on said target of said sensing means, said projecting system comprising a means for superposing the images of different areas of said inspected zone of the liquid, said projecting system including an objective lens and said means for superposing the images comprising two flat parallel reflecting surfaces facing each other and positioned parallel to the axis of said objective lens of said projecting system between said target of said sensing element and said objective lens so that the images of at least of some of said areas of said inspected zone of the liquid are projected on said target of said sensing element after being reflected from one or both of said reflecting surfaces; and a register means for registering the signal at said output of said radiation receiving device.

2. An apparatus according to claim 1, further comprising a radiation filter positioned between said radiation source and said objective lens of said projecting system and made so that the transparency of its portions traversed by the rays falling on said target of said sensing element of said radiation receiving device after being reflected from at least one of said reflecting surfaces of said means for superposing the images is greater than the transparency of the portion of said filter traversed by the rays falling on said target of said sensing element directly through said objective lens without reflection from any of said reflecting surfaces, and the transparency of the portions of said filter traversed by the rays falling on said target of said sensing element after a greater number of reflections is greater than the transparency of the portions of said filter traversed by the rays falling on said target of said sensing element after a smaller number of reflections.

3. An apparatus according to claim 1, further comprising at least one additional radiation source, said radiation sources being positioned so that the intensity of radiation incident on that area of said inspected zone of the liquid the image of which is projected on said target of said sensing element of said radiation source directly through said objective lens without reflection from any of said reflecting surfaces of said means for superposing the images is less than the intensity of radiation incident on that area of said inspected zone the image of which is projected on said target of said sensing element after being reflected from any of said reflecting surfaces, and the intensity of radiation incident on that area of said inspected zone the image of which is projected on said target of said sensing element is the greater, the greater is the number of reflections undergone by the image of this area before being projected on said target of said sensing element.

4. An apparatus according to claim 1, further comprising an optical filter positioned between said radiation source and said container and having a transparency varying along the height of said optical filter, so that the transparency of portions traversed by rays illuminating a middle portion of said container is less than the transparency of portions traversed by rays illuminating outer portions of said container.

* * * * *